United States Patent
Leung et al.

[11] Patent Number: 5,945,677
[45] Date of Patent: Aug. 31, 1999

[54] FOCUSED ION BEAM SYSTEM

[75] Inventors: Ka-Ngo Leung, Hercules; Richard A. Gough, Kensington; Qing Ji; Yung-Hee Yvette Lee, both of Berkeley, all of Calif.

[73] Assignee: The Regents of the University of California, Oakland, Calif.

[21] Appl. No.: 09/225,996

[22] Filed: Jan. 5, 1999

Related U.S. Application Data

[60] Provisional application No. 60/081,366, Apr. 10, 1998.
[51] Int. Cl.$^6$ ........................................................ H01J 3/18
[52] U.S. Cl. .................................. 250/396 R; 250/423 R; 250/398
[58] Field of Search .......................... 250/396 R, 423 R, 250/398, 309

[56] References Cited

U.S. PATENT DOCUMENTS 4,629,898  12/1986  Orloff et al. ........................ 250/396 R Primary Examiner—Kiet T. Nguyen
Attorney, Agent, or Firm—Henry P. Sartorio

[57] ABSTRACT

A focused ion beam (FIB) system produces a final beam spot size down to 0.1 μm or less and an ion beam output current on the order of microamps. The FIB system increases ion source brightness by properly configuring the first (plasma) and second (extraction) electrodes. The first electrode is configured to have a high aperture diameter to electrode thickness aspect ratio. Additional accelerator and focusing electrodes are used to produce the final beam. As few as five electrodes can be used, providing a very compact FIB system with a length down to only 20 mm. Multibeamlet arrangements with a single ion source can be produced to increase throughput. The FIB system can be used for nano-lithography and doping applications for fabrication of semiconductor devices with minimum feature sizes of 0.1 μm or less.

20 Claims, 7 Drawing Sheets

5,945,677

FOCUSED ION BEAM SYSTEM

RELATED APPLICATIONS

This application claims priority of Provisional Application Ser. No. 60/081,366 filed Apr. 10, 1998.

GOVERNMENT RIGHTS

The United States Government has rights in this invention pursuant to Contract No. DE-AC03-76SF00098 between the United States Department of Energy and the University of California.

BACKGROUND OF THE INVENTION

The invention relates generally to ion beams and more particularly to compact focused ion beam systems for generating ion beams of various elements with ion beam output currents of 1 $\mu$A or greater and final beam spot size down to 0.1 $\mu$m or less for lithography and doping applications.

As the dimensions of semiconductor devices are scaled down in order to achieve ever higher level of integration, optical lithography will no longer be sufficient for the needs of the semiconductor industry. Alternative "nanolithography" techniques will be required to realize minimum feature sizes of 0.1 $\mu$m or less. Therefore, efforts have been intensified worldwide in recent years to adapt established techniques such as X-ray lithography, extreme ultraviolet lithography (EUVL), and electron-beam (e-beam) lithography, as well as newer techniques such as ion projection lithography (IPL) and atomic-force-microscope (AFM) lithography, to the manufacture of 0.1 $\mu$m-generation complementary metal-oxide-semiconductor (CMOS) technology. Significant challenges exist today for each of these techniques: for X-ray, EUV, and projection ion-beam lithography, there are issues with complicated mask technology; for e-beam and AFM lithography, there are issues with low throughput.

Focused ion beam (FIB) patterning of films is a well-established technique (e.g. for mask repair), but throughput has historically been a prohibitive issue in its application to lithographic processes in semiconductor manufacturing. A scanning FIB system would have many advantages over alternative nanolithography technologies if it can be made practical for high volume production. Such a system could be used for maskless and direct (photoresist-less) patterning and doping of films in a semiconductor fabrication process. The main problem with present FIB systems is low current, on the order of nanoamps or picoamps. It would be desirable to have a compact FIB system which produces ion beam currents on the order of microamps. It would also be necessary to focus the beam down to sub-micron spot sizes.

SUMMARY OF THE INVENTION

Accordingly it is an object of the invention to provide a focused ion beam (FIB) system which has an output current on the order of microamps.

It is also an object of the invention to provide a FIB system which has a final beam spot size down to 0.1 $\mu$m or less.

The invention is a focused ion beam (FIB) system which produces a final beam spot size down to 0.1 $\mu$m or less and an ion beam output current on the order of microamps, and an electrode combination for an ion source which allows the extraction of microamp currents. The FIB system of the invention increases ion source brightness by properly configuring the first (plasma) and second (extraction) electrodes. Additional accelerator and focusing electrodes are used to produce the final beam. In a preferred embodiment, only five electrodes are used, providing a very compact FIB system with a length of only 20 mm. Multiple beamlet systems can be produced to increase throughput. The invention can be used for nanolithography and doping applications for fabrication of semiconductor devices with minimum feature sizes of 0.1 $\mu$m or less.

DETAILED DESCRIPTION OF THE INVENTION

Figure 1:
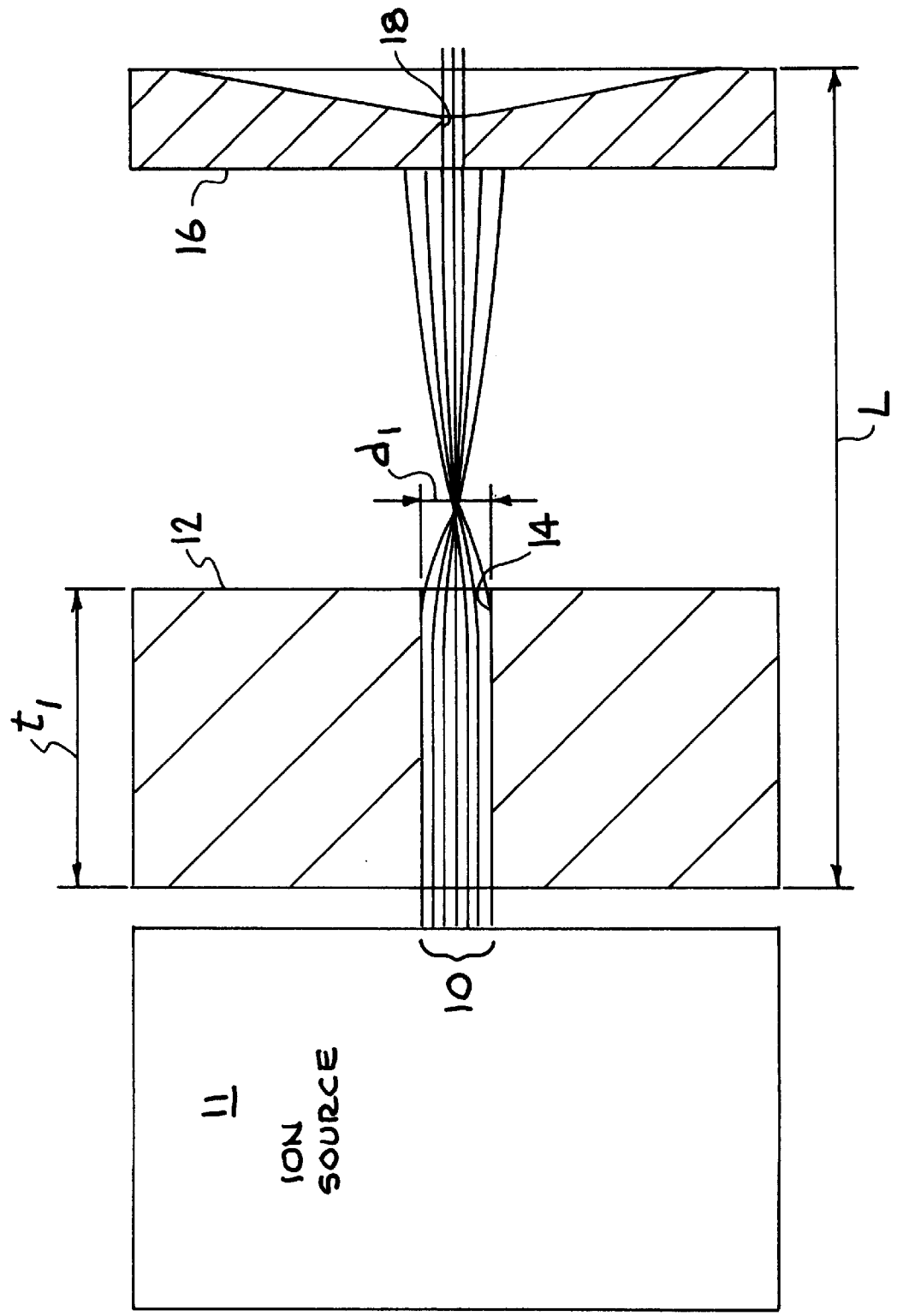
FIG. 1 illustrates the problem of extracting high beam current from a prior art exit/extraction electrode system.

FIG. 1 illustrates the typical configuration of the exit and extraction electrodes of a prior art ion source. A conventional focused ion beam system using this electrode configuration will inherently produce a very low ion current, making the source unsuitable for ion beam lithography because of the low throughput.

Ions are produced in a plasma generation region 10 of an ion source 11 which may be of conventional design. Conventional multicusp ion sources are illustrated by U.S. Pat. Nos. 4,793,961; 4,447,732; 5,198,677, which are herein incorporated by reference. Copending application Ser. No. 09/187,540 filed Nov. 6, 1998, which is herein incorporated by reference, describes a preferred ion source with a coaxial magnetic filter which has a very low energy spread. A first electrode 12, also known as the plasma electrode or exit electrode or beam forming electrode, is positioned adjacent to plasma generation region 10. First electrode 12 has an aperture 14 formed therein through which ions are drawn from the ion generation region 10. Electrode 12 has a thickness $t_1$, e.g. 1.6 mm, and is charged to a high voltage, e.g. 50 kV. Aperture 14 has a small diameter $d_1$, e.g. 0.2 mm. Because of the small aperture diameter and the relatively large electrode thickness, the aspect ratio $AR=d_1/t_1$ is small, e.g. 0.2/1.6=0.125.

A second electrode 16, known as the extraction electrode, is positioned in a spaced relationship with first electrode 12, e.g. L=4.8 mm. Electrode 16 contains an aperture 18 aligned with aperture 14, and is charged to a high voltage, e.g. 43 kV.

A relatively large ion current is produced in plasma generation region 10 and incident upon aperture 14 of electrode 12, e.g. $I_{in}$=120 $\mu$A. However, because of the low aspect ratio of aperture 14, the electric field produced by extraction electrode 16 cannot penetrate very far into aperture 14 to extract the ions and most of the ions are stopped by the electrode 12. Thus the output current from aperture 14 is very small, e.g. $I_{out}$=6 nA. The ratio $I_{out}/I_{in}$=1/20,000, i.e. only 0.005% of the ion current produced by the source gets through the low aspect ratio exit aperture. Since the diameter of aperture 18 in extraction electrode 16 is smaller than $d_1$, even less of $I_{out}$ gets through second electrode 16 into the rest of the FIB system.

Figure 2:
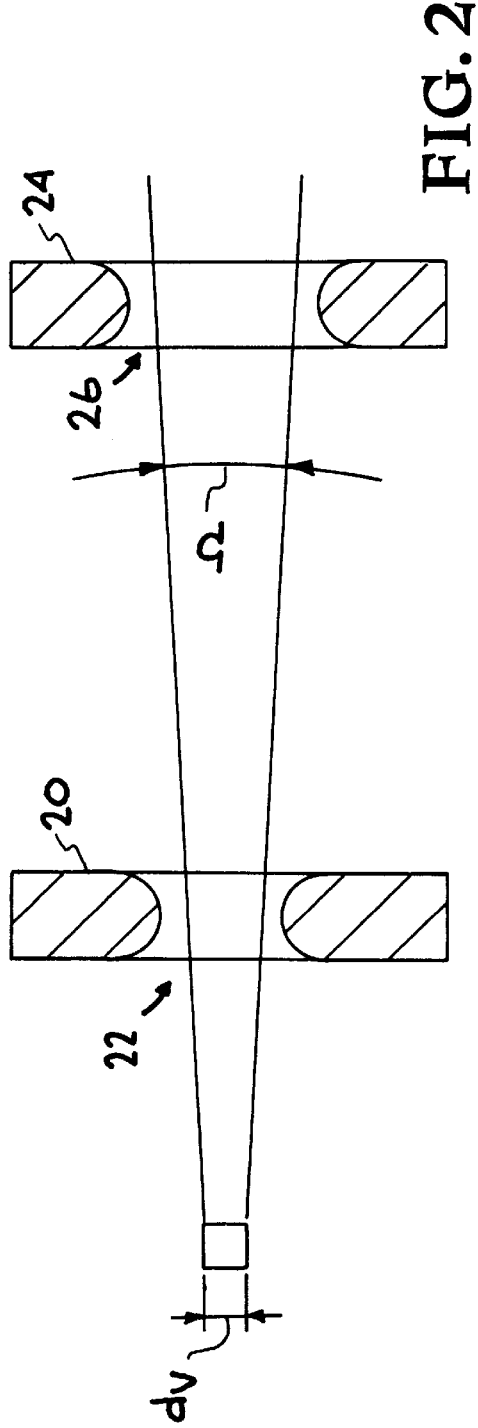
FIG. 2 illustrates the geometry to calculate the spectral brightness of an ion source.

The spectral brightness of the ion source is dependent on the ion source output current I, and the geometry of the source, as shown in FIG. 2. The relationship is $B_S=I_\Omega/d_v\Delta E$ where $B_S$ is spectral brightness $I_\Omega=I/\Omega$ is the angular current density (I is the output ion current and $\Omega$ is the beam solid angle), $d_v$ is the virtual source size, and $\Delta E$ is the energy spread of the ion source.

The parameters which determine brightness are highly dependent on the electrode geometry. The thickness and spacing of electrodes 20, 24 and the diameters of apertures 22, 26 affect $d_v$, $\Omega$ and I. But merely decreasing the size of aperture 22 does not increase brightness because of the aspect ratio problem.

A focused ion beam (FIB) system 30 according to the invention is formed of three sections or stages 32, 34, 36 as shown in FIGS. 3A–D. An ion beam 38 produced by an ion source or plasma generator 31 propagates through FIB system 30 to produce a focused output beam 40 which has a spot size down to 1 $\mu$m or less and a current greater than 1 $\mu$A. Plasma generator 31 is similar to ion source 11 of FIG. 1, and multicusp sources like those previously cited may be used. In particular source 30 may include a coaxial magnetic filter 33. The final beam 40 is incident on a workpiece or substrate 35, e.g. a silicon wafer, which is being processed. Substrate 35 is held on a mount 37 which may be translated relative to the beam position as an alternative to scanning the beam over the substrate 35.

Ion extraction section 32 is formed of a first electrode 42 and a spaced second electrode 44. Electrodes 42, 44 are the exit and extractor electrodes respectively of the ion source 31. Electrode 42 has an aperture 43 and electrode 44 has an aperture 45. The diameter of aperture 43 is much greater than the diameter of aperture 45, e.g. 0.5 mm and 0.08 mm respectively. Electrode 42 also has a tapered surface 46 which tapers in toward aperture 43, e.g. forming a knife edge, so that the aspect ratio (aperture diameter/electrode thickness) is greatly increased. Therefore, most of the ion current in the input beam 38 will pass through aperture 43 in exit electrode 42.

Extraction electrode 44 is at a slightly lower high voltage than exit electrode 42, e.g. 47 kV compared to 50 kV, and accelerates the ions toward aperture 45. A substantial amount of the beam current will pass through aperture 45 because of the kinetic energy of the ions, even though aperture 45 is narrower than aperture 43. Ion currents of 1 $\mu$A or greater can be extracted.

The ion beam from extraction section 32 then passes through an accelerator section 34 which is made up of a plurality of accelerator electrodes, e.g. four accelerator electrodes 48, 49, 50, 51, which are at successively lower voltages to further accelerate the ions, e.g. 44 kV, 36 kV, 24 kV, 0 kV.

The ion beam from accelerator section 34 passes through focusing section (Einzel lens) 36. Einzel lens 36 is formed of three electrodes 52, 53, 54 with the two end electrodes 52, 54 at 0 kV and the center electrode at a high voltage e.g. 30 kV. The end electrodes 52, 54 of Einzel lens 36 are split electrodes.

Figure 4A:
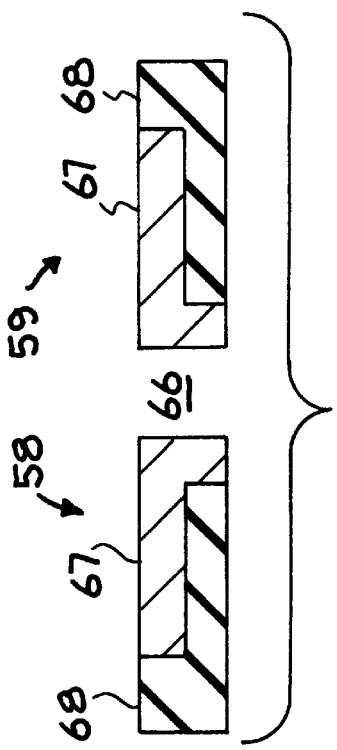
FIGS. 4A, B are end and sectional views of a split electrode for an Einzel lens.
Figure 4B:
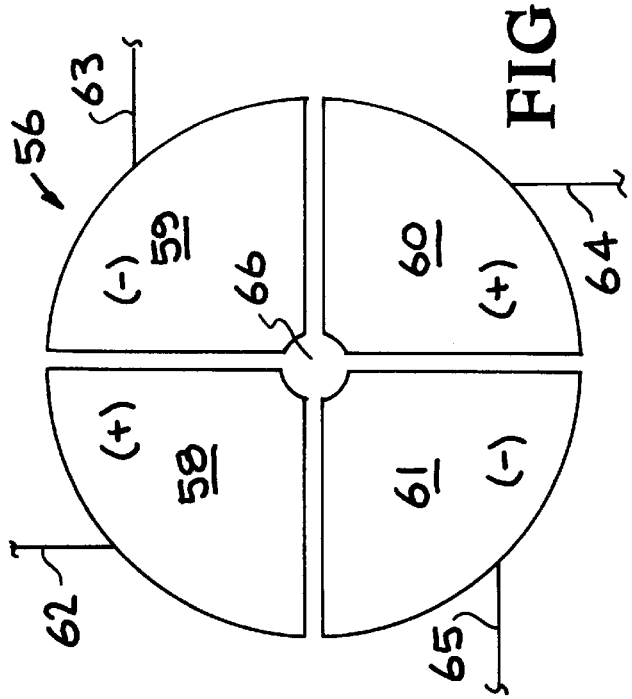

A split electrode 56, as shown in FIG. 4A, which can be used in Einzel lens 36, is formed of four electrically isolated segments 58, 59, 60, 61. By applying voltages to the electrode segments through electrical connections 62, 63, 64, 65, a beam passing though central aperture 66 may be deflected or scanned, as well as focused. The electrode segments, e.g. 58, 59, are formed of a copper or other metal electrode portion 67 on an insulator 68, as shown in FIG. 4B.

Figure 3A:
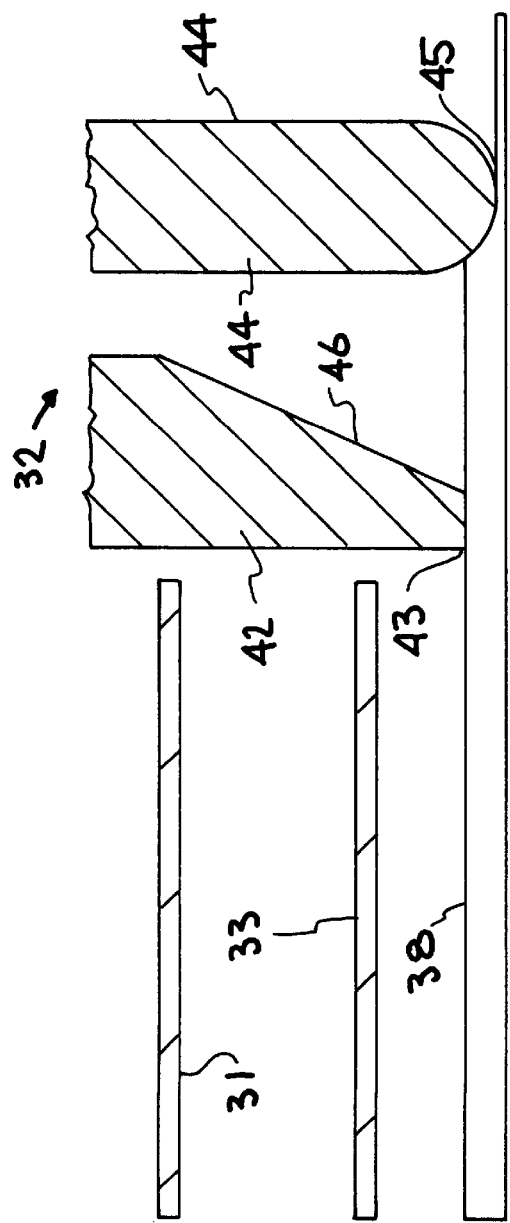
FIGS. 3A–C show segments of an FIB electrode system according to the invention.
Figure 3B:
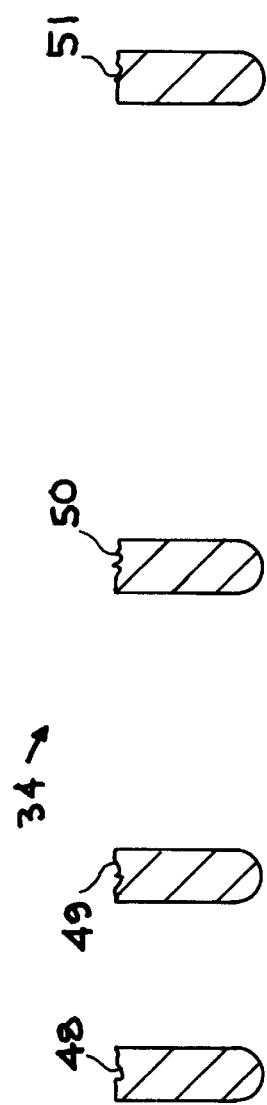
Figure 3C:
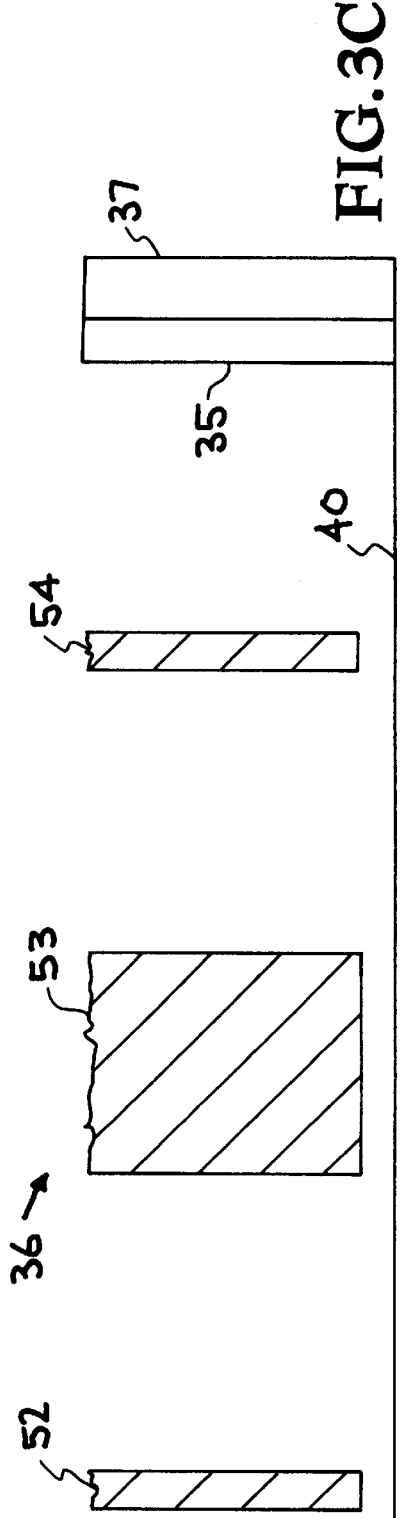
Figure 3D:
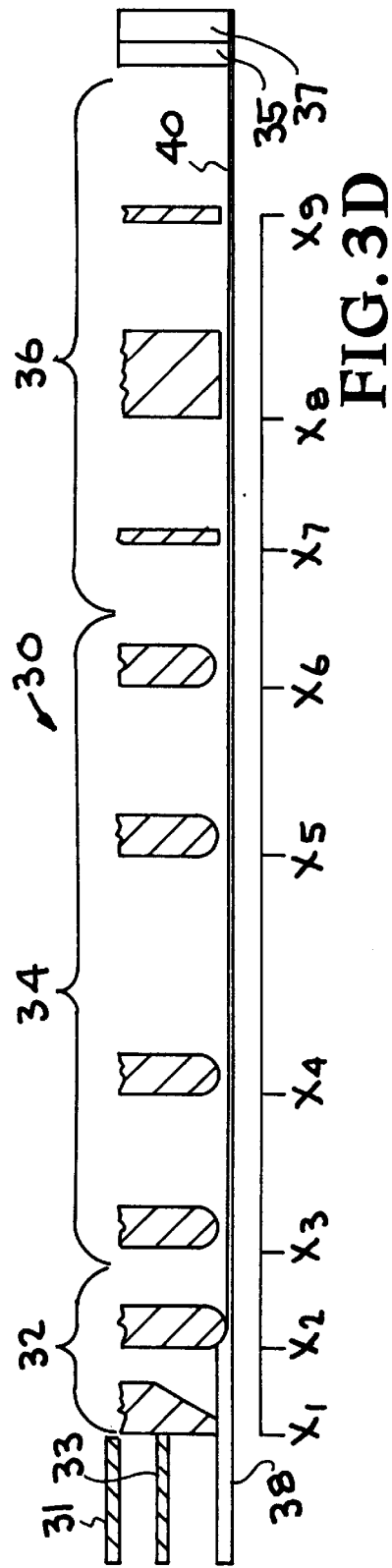
FIG. 3D shows the entire system.

An illustrative embodiment of electrode system 30 of FIG. 3D is made up of 9 electrodes which have their leading edges at positions $x_1$=0 mm, $x_2$=1.5 mm, $x_3$=3.25 mm, $x_4$=6 mm, $x_5$=10.25 mm, $x_6$=17 mm, $x_7$=20 mm, $x_8$=22.25 mm, $x_9$=25.75 mm. The widths of the first 6 electrodes are 0.75 mm, except that the first electrode has a tapered shape which is much narrower at the central aperture. The widths of the seventh and ninth electrodes (first and third electrodes of the Einzel lens) are 0.25 mm, and the width of the eighth electrode (second electrode of the Einzel lens) is 1.5 mm. The radius of the central aperture of the first electrode is 0.25 mm, the radius of the central aperture of the second electrode is 0.04 mm, the radius of the apertures of the third through sixth electrodes is 0.10 mm, and the radius of the apertures of the seventh through ninth electrodes (Einzel lens) is 0.15 mm. With these dimensions, a compact focusing electrode system only 26 mm in length is produced. With these parameters and illustrative voltages, an output beam with a radius of 1 $\mu$m can be produced.

Figure 5:
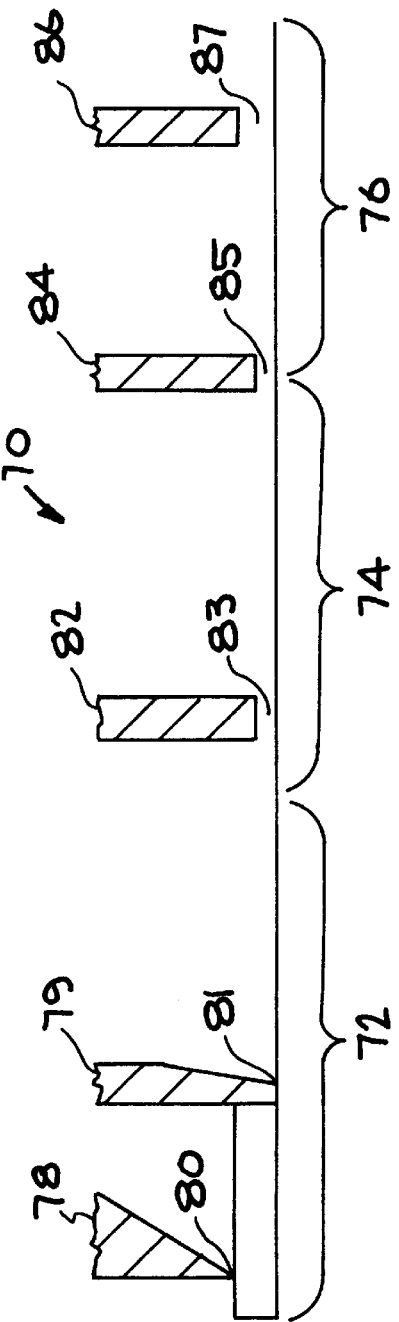
FIG. 5 illustrates a more compact five-electrode configuration for a FIB system according to the invention.

However, FIG. 5 illustrates a more compact FIB system 70 which is formed of three sections 72, 74, 76. Extraction section 76 is formed of an exit electrode 78 and an extraction electrode 79 which are similar to section 32 of FIG. 3A. A high aspect ratio (aperture diameter to electrode thickness) large radius aperture 80 is formed in exit electrode 78 so most of the ion current will pass. Exit electrode 78 tapers to a knife-edge at aperture 80 to increase the aspect ratio. Extraction electrode 79 has a narrower diameter aperture 81.

The acceleration and focusing sections 74, 76 are formed of a total of three electrodes 82, 84, 86 which have respective central apertures 83, 85, 87. In an illustrative embodiment the radius of aperture 80 is 0.5 mm, the radius of aperture 81 is 0.06 mm, and the radius of apertures 83, 85, 87 is 0.25 mm. The width of electrode 78 tapers down to almost a point at aperture 80, and the widths of the other electrodes are 0.05 mm. The total length of the FIB system 70 is only 20 mm.

The fast scanning FIB system of the invention possesses several unique features. First, a multicusp ion source, rather than a liquid metal ion source, will be employed. A typical multicusp source is comprised of three main elements: the source chamber or the anode walls, the filament cathode, and the extraction electrodes. The external surface of the chamber is surrounded by columns of permanent magnets which form multicusp fields for primary electron and plasma confinement. The cusp fields are localized near the chamber wall, leaving a large portion of the source free for magnetic fields. As a result, this type of ion source can generate large volumes of uniform and quiescent plasma. By installing a magnetic filter in the source, the axial ion energy spread can be reduced to values below 3 eV and even below 1 eV with a coaxial filter. The output current density is high (>250 mA/cm$^2$) for steady-state operation and the source can produce an ion beam of nearly any element.

Second, the accelerator column will be made up of nine small electrodes. Beam focusing is achieved by means of an Einzel lens. A 50 kV accelerator design can produce beam spot size of approximately 1 $\mu$m with an input current density of 250 mA/cm$^2$. The output beam current is approximately 12 $\mu$m in this case. The final ion beam energy can be varied by changing the number of electrodes in the column. Better accelerator designs can achieve much smaller beam spot size. The accelerator electrodes will be made out of copper. These will be sandwiched between electrically insulating material before the small apertures are drilled by using either electron or laser beams.

Third, the ion beams in this system will be scanned in the X and Y directions by a pair of split electrodes which also form part of the Einzel lens structure. The scan time is on the order of 10 ns for a beam displacement of several cm. The advantage of the scheme over conventional parallel-plate deflectors is that both beam focusing and deflection can be achieved simultaneously. The total length of the entire accelerator column would be about 3 cm, which is very much smaller than any conventional FIB tool based on liquid metal ion sources.

The multicusp ion source can generate atomic or molecular ion beams of nearly any element. In particular, steady-state beams of phosphorus, boron, and even metallic ions such as copper, titanium, tantalum, and tungsten have been produced by sputtering techniques. The filament cathode in the multicusp source chamber can be replaced by a radio-frequency (RF) induction coil to produce a plasma by induction discharge. In normal RF source operation, the antenna is covered by a thin layer of insulating material such as glass or porcelain. If the antenna is operated without an insulative coating, the coil material can be sputtered away and then ionized by the background energetic electrons. The resulting metallic ions will form part of the extracted ion beam.

The single-beam scanning FIB system can be used in a multiple beamlet system. There are two possible approaches for multi-beamlet generation. One approach is to use a single ion source together with a multi-aperature accelerator column. The multicusp source is ideal for this approach because it provides a large uniform plasma. A large number of beamlets can be extracted from the uniform plasma density region, with their separation determined by the desired die spacing on the wafer substrate. The accelerator electrode would be a stacked multilayer structure containing many apertures (one beamlet for each die) operated with the same potentials.

Figure 6:
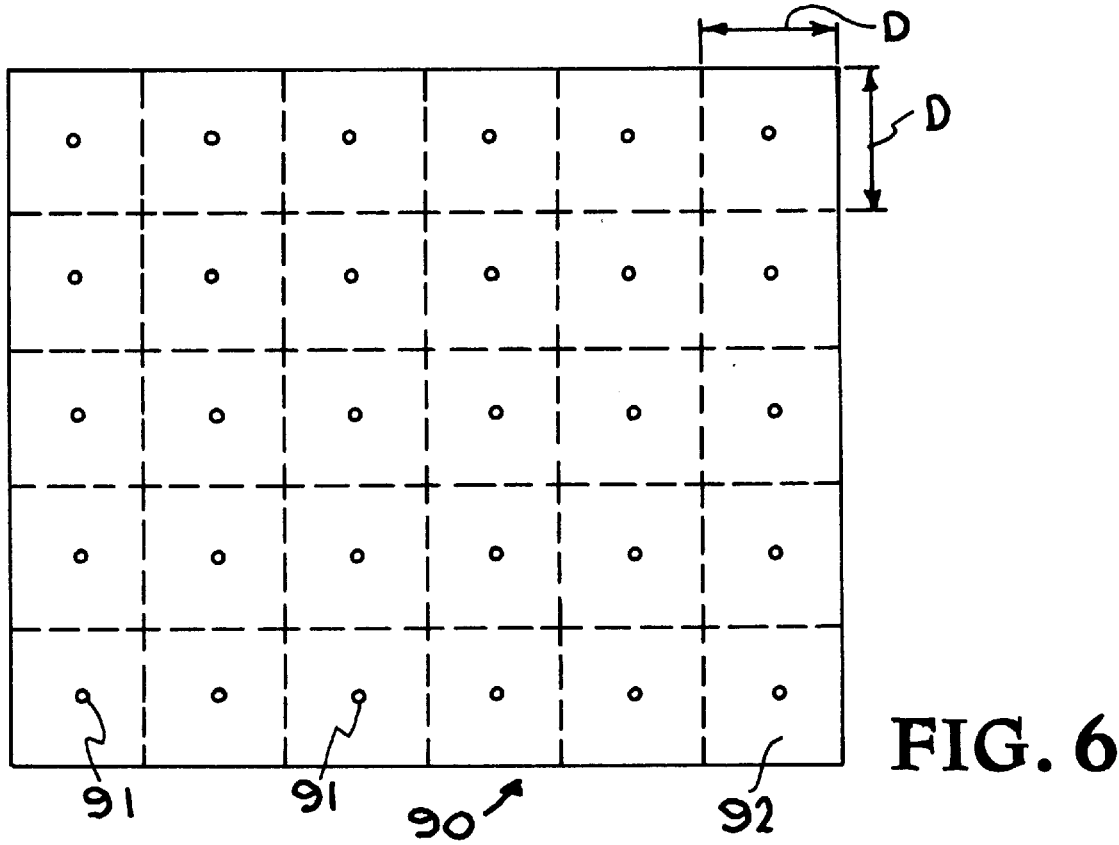
FIG. 6 shows a multiple beamlet system.

An array 90 of beam apertures 91 superposed over an array of dies 92 is shown in FIG. 6. The array 90 of beam apertures 91 may be used to extract ions from a single ion source. Adjacent beam apertures 91 are spaced apart by a distance D which corresponds to the die dimension. For example, a die 92 has dimensions D×D, e.g. 3 cm×3 cm. The individual beamlets which pass through the apertures 91 impinge on corresponding dies 92, one beamlet per die. The beamlets can be scanned over the dies, or the dies can be moved relative to the beamlets.

Figure 7:
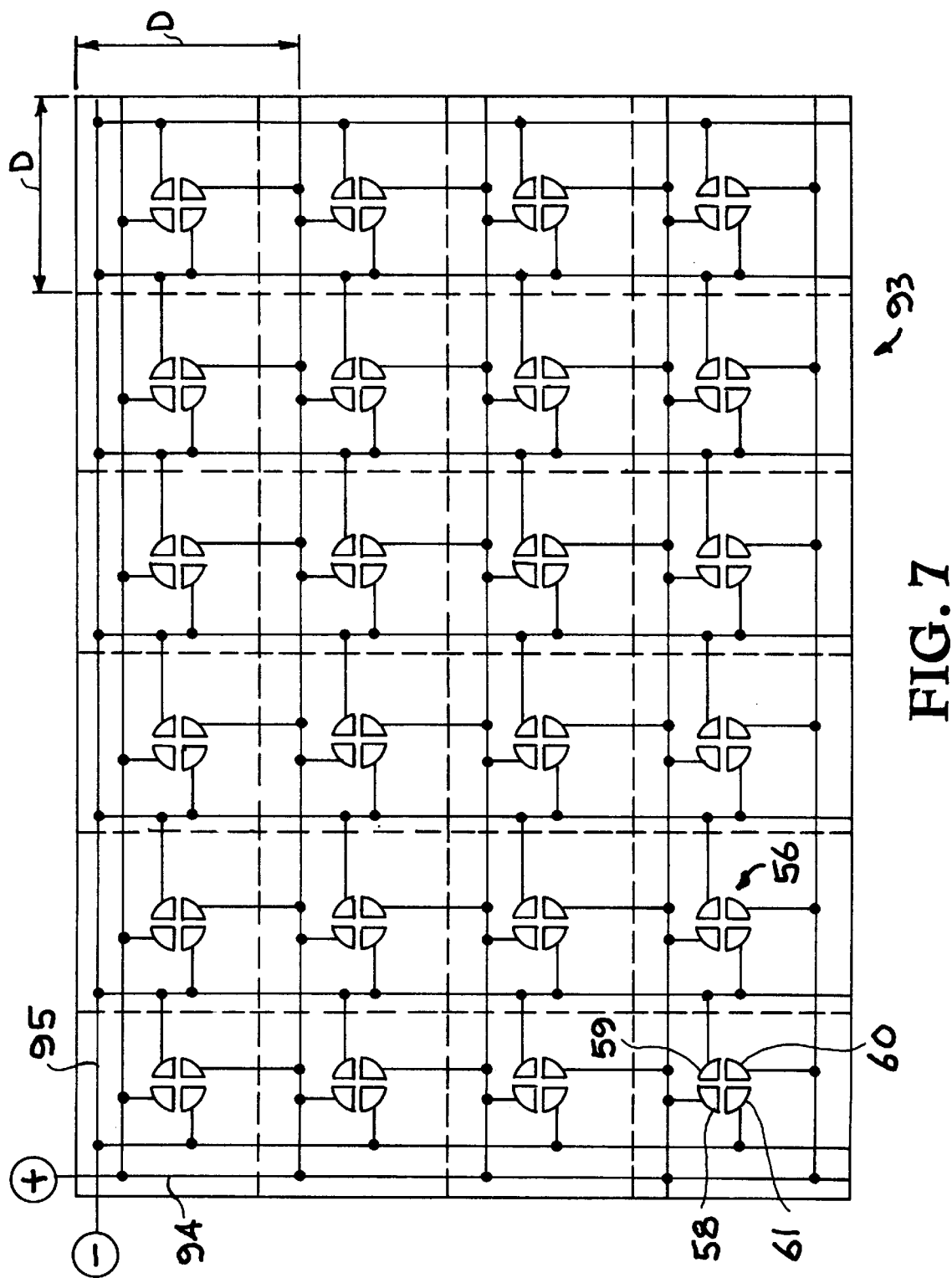
FIG. 7 shows the electrical connections to the split electrodes of the Einzel lenses of the multiple beamlet system of FIG. 6.

The two split electrodes (the first and the last electrodes) of the Einzel lens in a multiaperture array would be formed on an insulating board in a manner similar to that for printed circuit boards. FIG. 7 illustrates the electrical connections to the quadrants of the split electrodes so as to achieve beam scanning for each of the beamlets simultaneously. A plurality of split electrodes 56, similar to the split electrodes of FIG. 4A, form an array 93. Each electrode 56 has four quadrants or electrically isolated sections 58, 59, 60, 61. Array 93 includes a positive electrical bus 94 and a negative electrical bus 95 which are connected to a suitable power supply represented by the + and − symbols. The positive quadrants 58, 60 are electrically connected to positive bus 94 and the negative quadrants 59, 61 are electrically connected to the negative bus 95. Thus by applying appropriate voltage signals to the busses 94, 95, all the beamlets can be simultaneously controlled to scan to the same positions of corresponding dies.

The second approach for multiple beamlet generation is to employ multiple FIB units. Operation of this multi-ion-gun arrangement would be very similar to the electron gun micro-columns being developed by T. H. P. Chang at IBM. In this case, many accelerator columns would be used, each operated with a single ion source.

Figure 8:
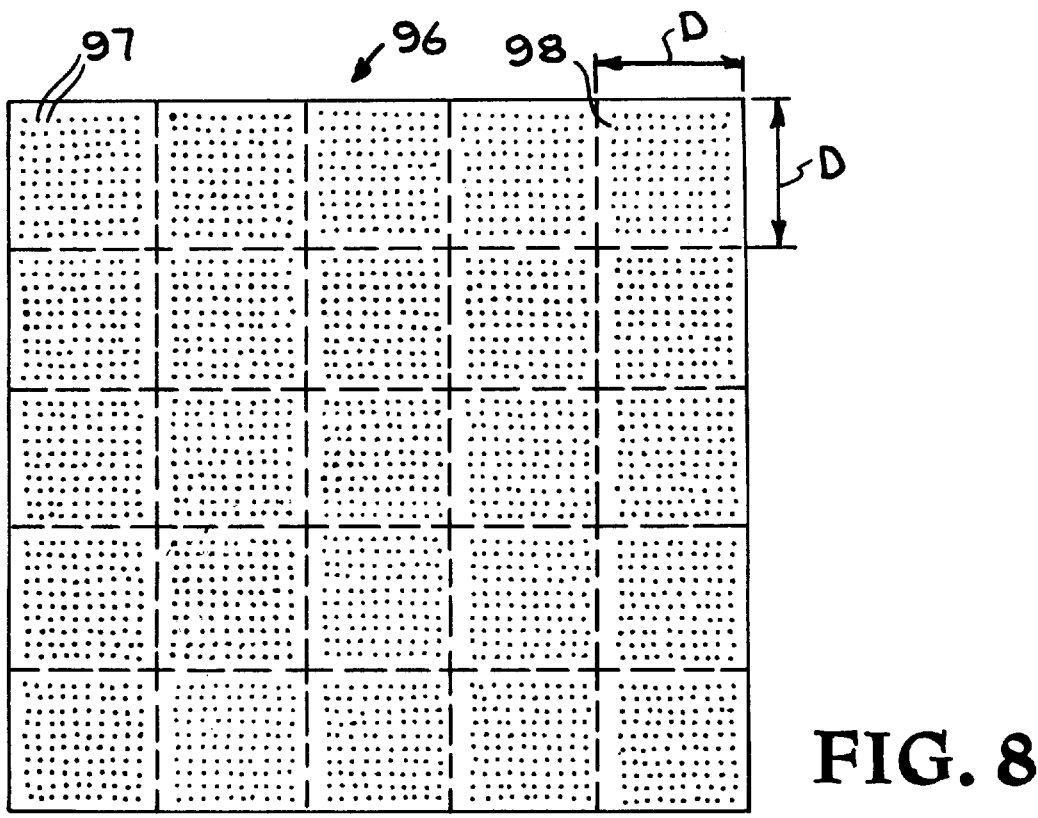
FIG. 8 shows an arrangement of 100 beamlets in a processing area of 3 cm×3 cm.

Further reductions in processing time can be achieved by increasing the number of beamlets within each die area. FIG. 8 shows a possible arrangement of N×N=100 beamlets inside an area of D×D, e.g. 3 cm×3 cm. The array 96 of beam apertures 97 now contains N×N apertures corresponding to a single die 98 which has dimensions D×D. All N×N beamlets which pass through a set of apertures 97 corresponding to a single die 98 will impinge on that die. The time to write an entire wafer could possibly be reduced to less than one second with this approach. In contrast to the prior arrangement, the N×N beamlets in this case would have to be switched on and off independently at high speeds. This can be accomplished by turning the extraction voltage on the second electrode on and off individually. Beam scanning would be again performed by the Einzel lens system. The split electrodes of the Einzel lens system would need to be miniaturized.

Figure 9:
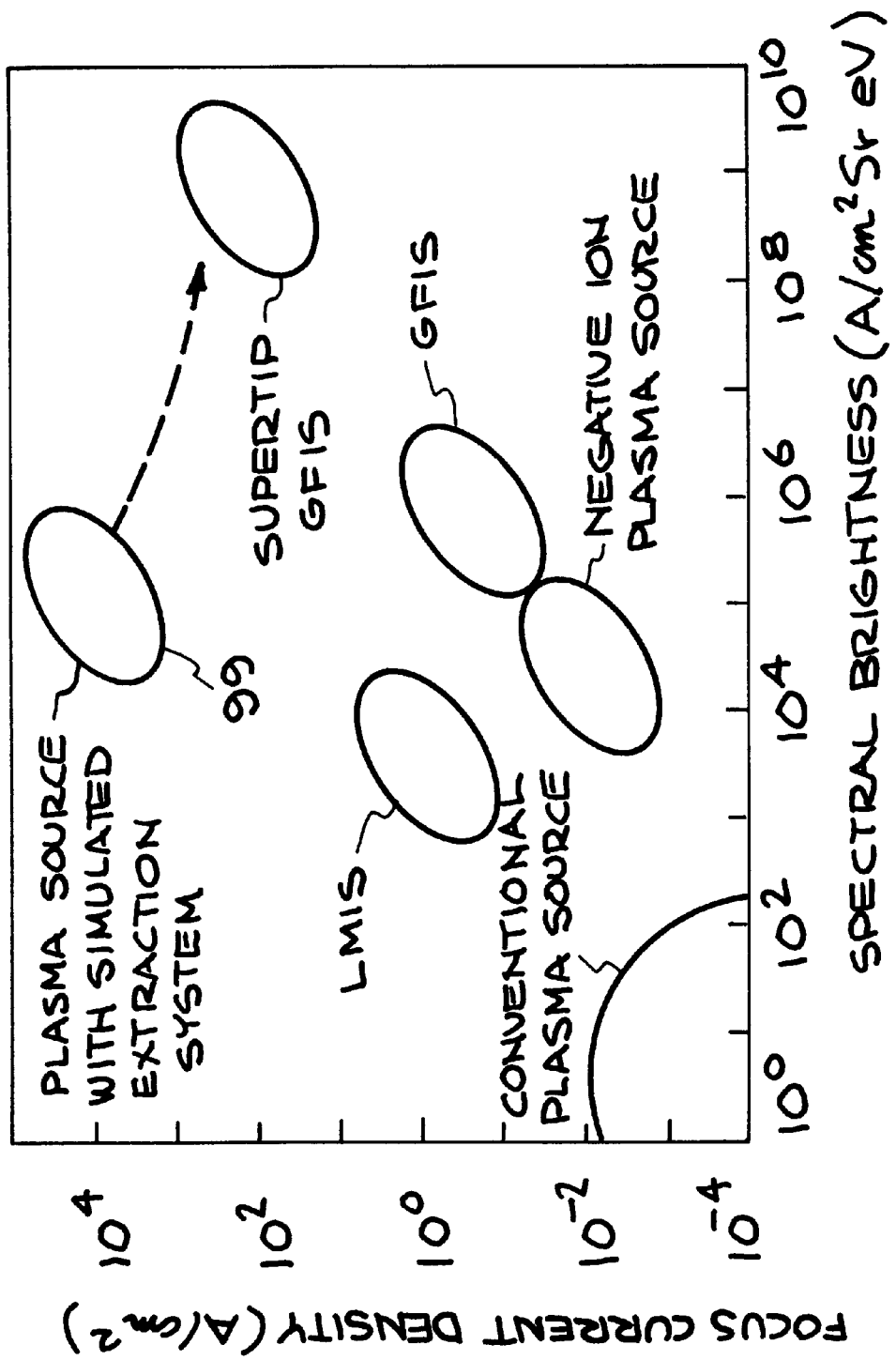
FIG. 9 is a comparison of ion source current density and spectral brightness of the present invention with prior art systems.

A comparison of the ion source current density and spectral brightness achieveable by the present invention and those of prior art systems is shown in FIG. 9. The present invention produces the highest density of any system, as represented by region 99. The present invention can be designed to produce a similar spectral brightness as the supertip gas field ion source (GFIS) system (as shown by the dashed arrow) and the advantage is that it is a far less complex system.

Changes and modifications in the specifically described embodiments can be carried out without departing from the scope of the invention which is intended to be limited only by the scope of the appended claims.

We claim:

1. An exit/extraction electrode combination for an ion source, comprising:

a first electrode positioned adjacent to the ion source and having a first aperture formed therein;

a second electrode in a spaced relation to the first electrode and having a second aperture formed therein and aligned with the first aperture, the first and second electrodes having voltages applied thereto to extract ions from the ion source through the first aperture and on through the second aperture;

wherein the ratio of the first aperture diameter to the first electrode thickness at the aperture is sufficiently large to produce an ion current through the first aperture of at least about 1 $\mu$A.

2. The electrode combination of claim 1 wherein the diameter of the first aperture is much greater than the diameter of the second aperture.

3. The electrode combination of claim 1 wherein the diameter of the first aperture is about 0.5–1.0 mm and the diameter of the second aperture is about 0.08–0.12 mm.

4. The electrode combination of claim 1 wherein the first electrode tapers to a knife-edge at the first aperture.

5. A focused ion beam system, comprising:
- a plasma generator which produces ions in a plasma generation region;
- a first electrode positioned adjacent to the plasma generation region and having a first aperture formed therein;
- a second electrode in a spaced relation to the first electrode and having a second aperture formed therein and aligned with the first aperture, the first and second electrodes having voltages applied thereto to extract ions from the plasma generation region through the first aperture and on through the second aperture;
- additional acceleration and focusing electrodes following the second electrode and having aligned apertures therethrough for accelerating and focusing ions extracted from the plasma generation region to produce a final ion beam;
- wherein the ratio of the first aperture diameter to the first electrode thickness at the aperture is sufficiently large to produce an ion current through the first aperture of at least about 1 $\mu$A.

6. The focused ion beam system of claim 5 wherein the plasma generator comprises a multicusp ion source.

7. The focused ion beam system of claim 6 wherein the plasma generator comprises a multicusp ion source with a coaxial magnetic filter.

8. The focused ion beam system of claim 5 wherein the diameter of the first aperture is much greater than the diameter of the second aperture.

9. The focused ion beam system of claim 5 wherein the diameter of the first aperture is about 0.5 mm to 1.0 mm and the diameter of the second aperture is about 0.08 mm to 0.12 mm.

10. The focused ion beam system of claim 5 wherein the first electrode tapers to a knife-edge at the first aperture.

11. The focused ion beam system of claim 5 wherein the final ion beam has a spot size of about 1 $\mu$m or less.

12. The focused ion beam system of claim 5 wherein the additional acceleration and focusing electrodes include a split electrode Einzel lens for scanning the final ion beam over a workpiece.

13. The focused ion beam system of claim 5 further comprising a translatable mount for holding a workpiece onto which the final ion beam is directed.

14. The focused ion beam system of claim 5 wherein the additional acceleration and focusing electrodes comprise three electrodes.

15. The focused ion beam system of claim 14 wherein the length of the five electrode system is about 20 mm.

16. The focused ion beam system of claim 5 wherein each electrode comprises a plurality of additional apertures formed therein for extracting multiple beamlets from the plasma generator.

17. The focused ion beam system of claim 16 wherein each beamlet is directed to a corresponding die.

18. The focused ion beam system of claim 16 wherein an N×N array of beamlets is directed to a corresponding die.

19. A method of producing a focused ion beam, comprising:
- generating a plasma;
- extracting ions from the plasma through a first aperture in a first electrode, the ratio of the first aperture diameter to the first electrode thickness at the aperture being sufficiently large to produce an ion current through the first aperture of at least about 1 $\mu$A;
- passing the ions extracted through the first aperture through a second aperture in a second electrode;
- passing the ions extracted through the second aperture through aligned apertures in additional acceleration and focusing electrodes.

20. The method of claim 19 further comprising configuring the electrodes to form a final ion beam spot size of about 1 $\mu$m or less.

* * * * *